(12) United States Patent
Paek et al.

(10) Patent No.: US 11,857,580 B2
(45) Date of Patent: Jan. 2, 2024

(54) *LACTOBACILLUS* HAVING ANTIMICROBIAL EFFECT ON *GARDNERELLA VAGINALIS* AND *CANDIDA ALBICANS*

(71) Applicants: MEDIOGEN CO., LTD., Chungcheongbuk-do (KR); Nam Soo Paek, Seoul (KR)

(72) Inventors: Nam-Soo Paek, Seoul (KR); Chang Ho Kang, Chungcheongbuk-do (KR)

(73) Assignee: Mediogen Co., Ltd., Chungcheongbuk-Do (KR)

( * ) Notice: Subject to any disclaimer, the term of this patent is extended or adjusted under 35 U.S.C. 154(b) by 125 days.

(21) Appl. No.: 16/850,587

(22) Filed: Apr. 16, 2020

(65) Prior Publication Data
US 2020/0345798 A1    Nov. 5, 2020

(30) Foreign Application Priority Data
May 3, 2019 (KR) .................. 10-2019-0052198

(51) Int. Cl.
| | | |
|---|---|---|
| *A61K 35/747* | (2015.01) | |
| *A61P 31/04* | (2006.01) | |
| *C12N 9/18* | (2006.01) | |
| *C12N 9/42* | (2006.01) | |
| *C12N 9/48* | (2006.01) | |

(52) U.S. Cl.
CPC ............ *A61K 35/747* (2013.01); *A61P 31/04* (2018.01); *C12N 9/18* (2013.01); *C12N 9/2445* (2013.01); *C12N 9/485* (2013.01); *C12Y 301/01* (2013.01); *C12Y 301/03002* (2013.01); *C12Y 302/0102* (2013.01); *C12Y 302/01021* (2013.01); *C12Y 302/01031* (2013.01); *C12Y 304/11001* (2013.01)

(58) Field of Classification Search
None
See application file for complete search history.

(56) References Cited

FOREIGN PATENT DOCUMENTS
EP    3636782 A1    4/2020

OTHER PUBLICATIONS

Yang, E. et al. Jan. 2018. Influence of culture media, pH and temperature on growth and bacteriocin production of bacteriogenic lactic acid bacteria. AMB Express 8(10): 1-14; specif. pp. 1, 2, 4, 5, 9, 11.*
Reale, A. et al. 2015. Tolerance of Lactobacillus casei, Lactobacillus paracasei and Lactobacillus rhamnosus strains to stress factors encountered in food processing and in the gastro-intestinal tract. Food Science and Technology 60: 721-728; specif. pp. 721, 722, 723.*
Charteris, W.P. et al. 2001. Quality control Lactobacillus strains for use with API 50CH and API ZYM systems at 37oC. Journal of Basic Microbiology 41(5): 241-251; specif. pp. 241, 242, 244, 245.*
Stefanovic, E. et al. Mar. 2018. Comparative genomic and metabolic analysis of three Lactobacillus paracasei cheese isolates reveals considerable genomic differences in strains from the same niche. BMC Genomics, Open Access, pp. 1-13; specif. pp. 2, 3, 6.*
Shazali, N. et al. 2014. Prevalence of antibiotic resistance in lactic acid bacteria isolated from the faeces of broiler chicken in Malayjsia. Gut Pathogens 6(1): 1-7; specif. pp. 1, 2, 4.*
Otto, R.A. et al. 1994. Cephalosporin antibiotics. ENT Journal 73(12): 900-913; specif. pp. 900, 903, 907.*
Bjorneholm, S. et al. 2002. Enumeration and identification of Lactobacillus paracasei subsp *paracasei* F19. Microbial Ecology in Health and Disease, Suppl. 3: 7-13; specif. pp. 7, 8, 9.*
Noverr, M.C. et al. 2004. Regulation of Candida albicans morphogenesis by fatty acid metabolites. Infection and Immunity 72(11): 6206-6210; specif. p. 6208.*
Aroutcheva, A. et al. 2001. Defense factors of vaginal lactobacilli. American Journal of Obstetrics and Gynecology 185: 375-379; specif. pp. 375, 377, 378 (Year: 2001).*
Pan, Meichen, et al., "Comparative Analysis of Lactobacillus gasseri and Lactobacillus crispatus Isolated From Human Urogenital and Gastrointestinal Tracts", Frontiers in Microbiology vol. 10, Article 3146 (Jan. 22, 2020).
Zhang, Qiuxiang , et al., "Comparative Genomics of Lactobacillus crispatus from the Gut and Vagina Reveals Genetic Diversity and Lifestyle Adaptation", Genes 11:360 (Mar. 27, 2020) 14 pages.

* cited by examiner

*Primary Examiner* — Michael Barker
*Assistant Examiner* — Sharon M. Papciak
(74) *Attorney, Agent, or Firm* — Myers Bigel, P.A.

(57) ABSTRACT

The present invention relates to a *Lactobacillus* strain having antimicrobial activity against *Gardnerella vaginalis* and *Candida albicans*, a culture medium of the strain, and a cell-free supernatant of the strain, and to an antimicrobial composition containing the same, a pharmaceutical composition for preventing or treating *Gardnerella vaginalis* infection or *Candida albicans* infection containing the same, a pharmaceutical composition for prevention or treatment of vaginitis containing the same, a health functional food for prevention or ameliorating of vaginitis containing the same, and a quasi-drug composition for prevention or amelioration of vaginitis containing the same. The *Lactobacillus paracasei* MG4272 strain in accordance with the present disclosure has excellent antimicrobial activity against *Gardnerella vaginalis* and *Candida albicans*, and has excellent acid resistance, bile resistance, autoaggregation ability and epithelial cell adhesion ability and is suitable for probiotics and thus may be used in various ways for the prevention or treatment of *Gardnerella vaginalis* infection, *Candida albicans* infection and vaginitis.

11 Claims, 5 Drawing Sheets
Specification includes a Sequence Listing.

[Figure 1]
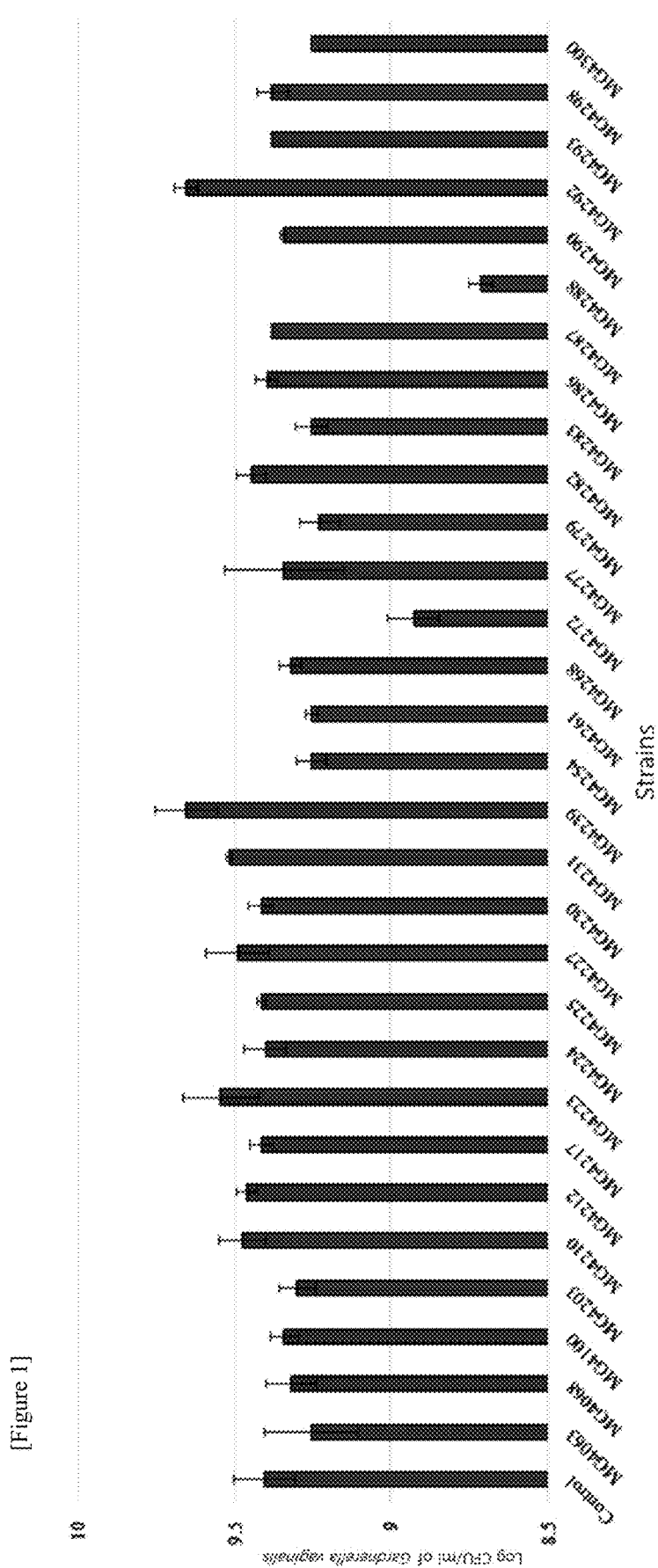

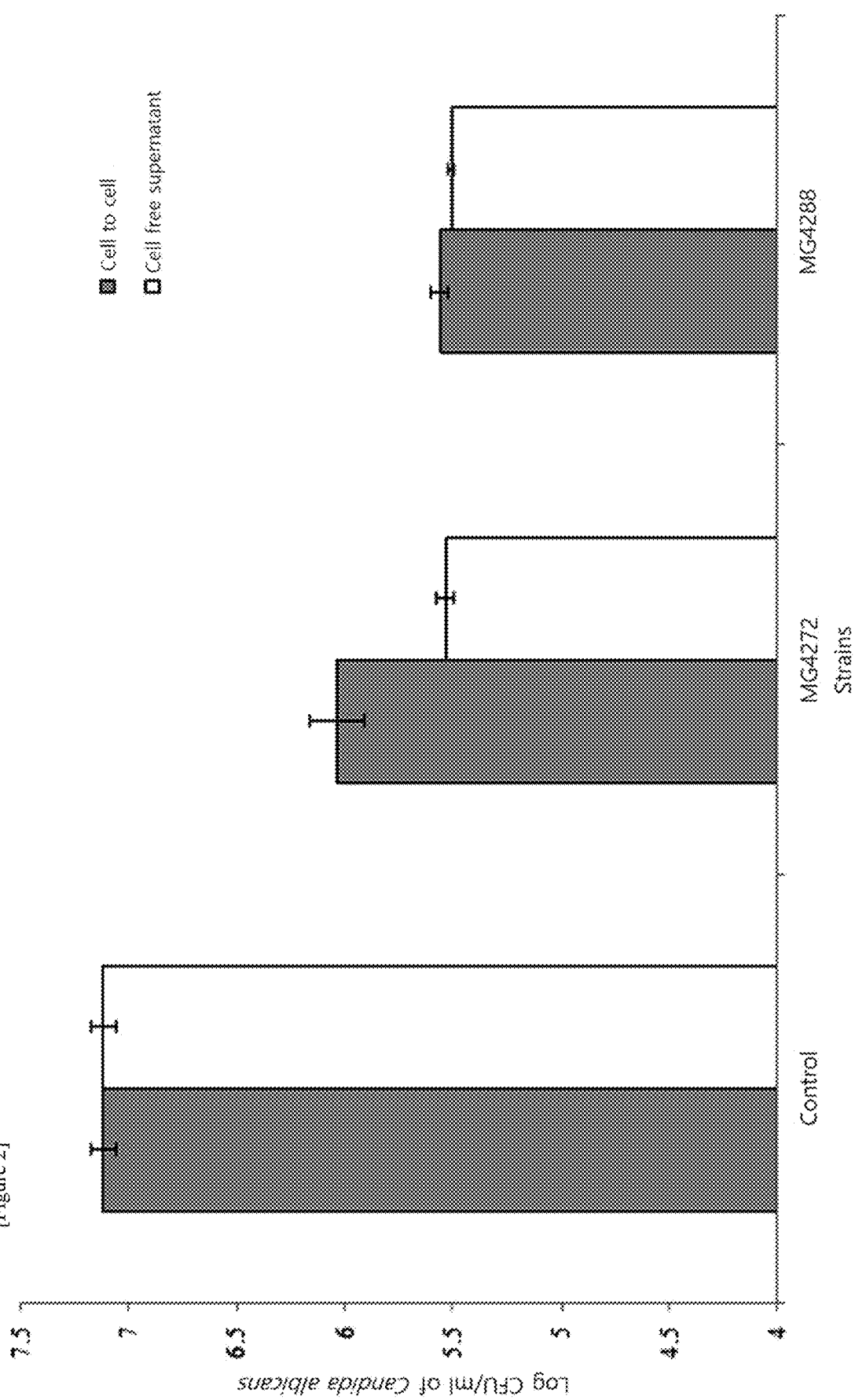
[Figure 2]

[Figure 3]
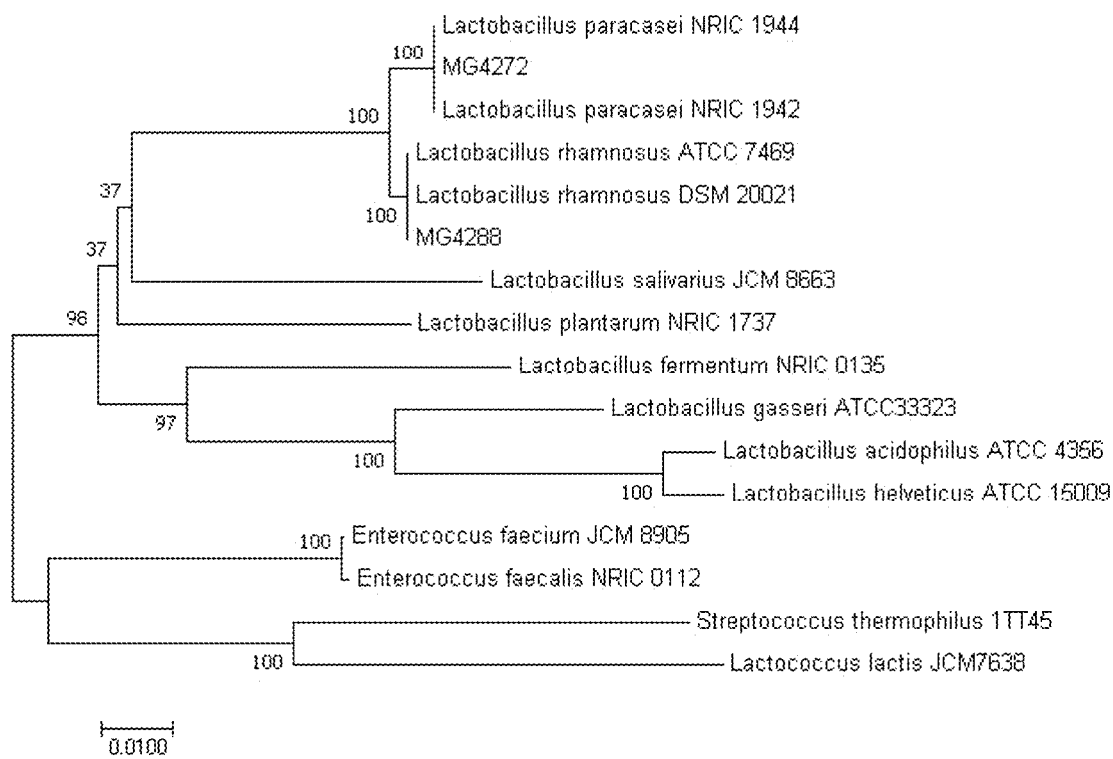
[Figure 4]
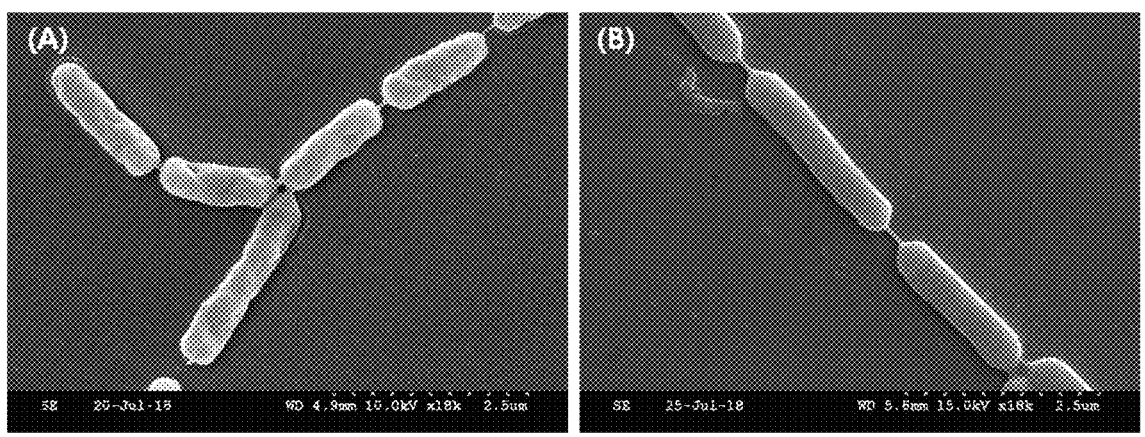

[Figure 5]
| Strains | Inhibition rate(%) | | Average | SD |
|---|---|---|---|---|
| L. paracasei MG4272 | 69.41 | 63.92 | 66.67 | 2.75 |
| L. paracasei MG5009 | 37.25 | 60.78 | 49.02 | 11.765 |
| L. paracasei MG5010 | 45.09 | 13.72 | 29.41 | 15.69 |
| L. paracasei MG5012 | 21.56 | 37.25 | 29.41 | 7.84 |
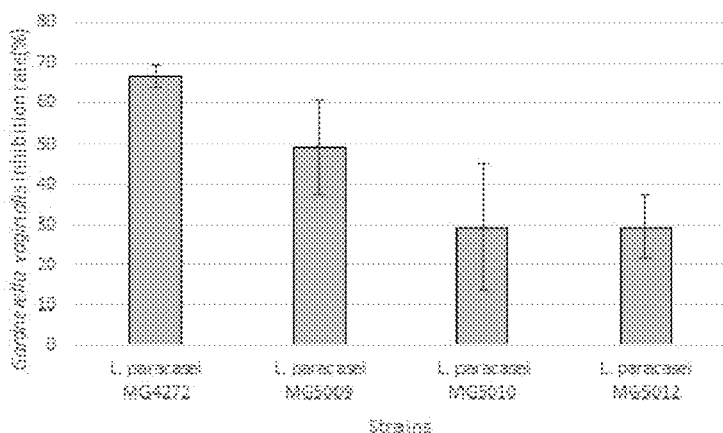
[Figure 6]
| Strains | Inhibition rate(%) | | Average | SD |
|---|---|---|---|---|
| L. rhamnosus MG4283 | 37.25 | 21.57 | 29.41 | 7.84 |
| L. rhamnosus MG4288 | 79.61 | 79.61 | 79.61 | 0 |
| L. rhamnosus MG4289 | 41.96 | 47.458 | 44.71 | 2.75 |
| L. rhamnosus MG4298 | 5.88 | 5.88 | 5.88 | 0 |
| L. rhamnosus MG5007 | 40.39 | 47.45 | 43.92 | 3.53 |
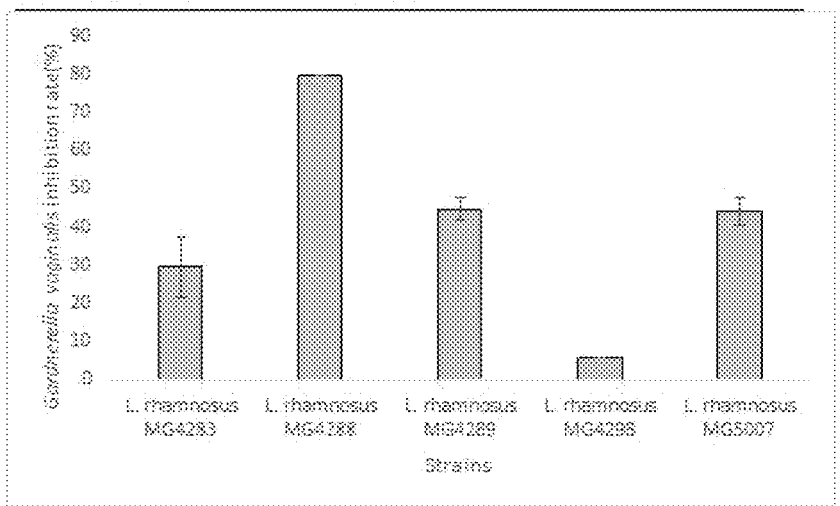

[Figure 7]
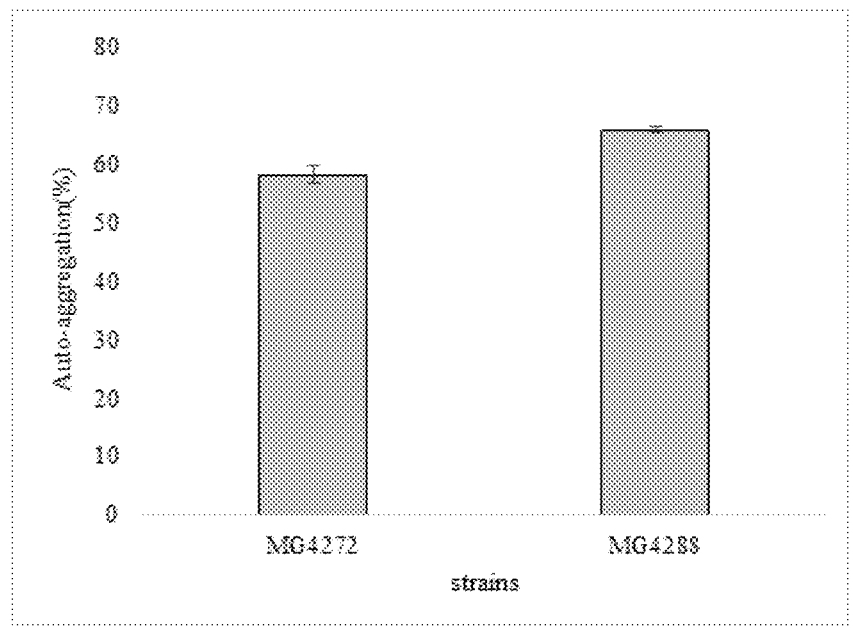
[Figure 8]
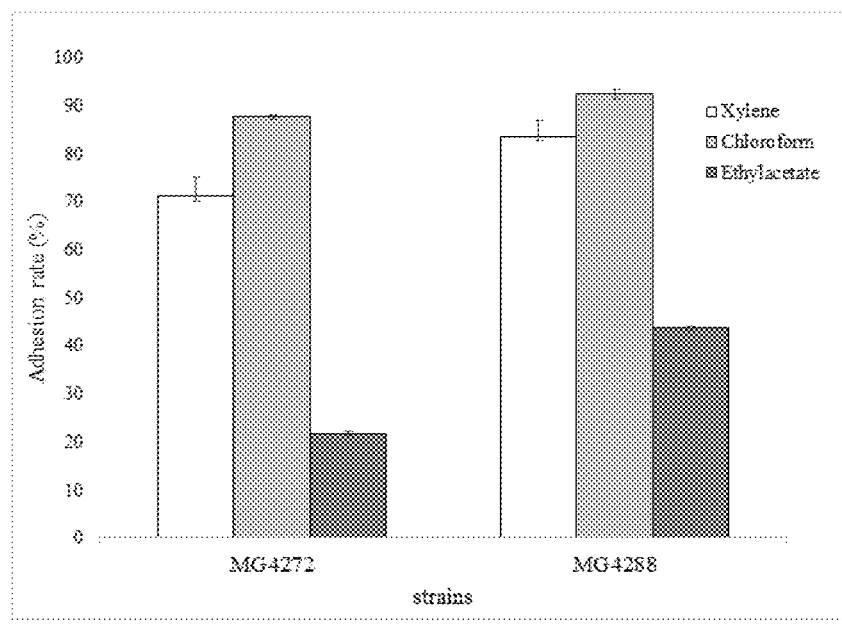

SEQUENCE LISTING

<160> NUMBER OF SEQ ID NOS: 2

<210> SEQ ID NO 1
<211> LENGTH: 1441
<212> TYPE: DNA
<213> ORGANISM: Lactobacillus paracasei

<400> SEQUENCE: 1

```
tgcagtcgaa cgagttctcg ttgatgatcg gtgcttgcac cgagattcaa catggaacga      60
gtggcggacg ggtgagtaac acgtgggtaa cctgcccctta agtgggggat aacatttgga     120
aacagatgct aataccgcat agatccaaga accgcatggt tcttggctga agatggcgt      180 aagctatcgc ttttggatgg acccgcggcg tattagctag ttggtgaggt aatggctcac      240
caaggcgatg atacgtagcc gaactgagag gttgatcggc cacattggga ctgagacacg      300
```

```
gcccaaactc ctacgggagg cagcagtagg gaatcttcca caatggacgc aagtctgatg      360
gagcaacgcc gcgtgagtga agaaggcttt cgggtcgtaa aactctgttg ttggagaaga      420
atggtcggca gagtaactgt tgtcggcgtg acggtatcca accagaaagc cacggctaac      480
tacgtgccag cagccgcggt aatacgtagg tggcaagcgt tatccggatt tattgggcgt      540
aaagcgagcg caggcggttt tttaagtctg atgtgaaagc cctcggctta accgaggaag      600
cgcatcggaa actgggaaac ttgagtgcag aagaggacag tggaactcca tgtgtagcgg      660
tgaaatgcgt agatatatgg aagaacacca gtggcgaagg cggctgtctg gtctgtaact      720
gacgctgagg ctcgaaagca tgggtagcga acaggattag ataccctggt agtccatgcc      780
gtaaacgatg aatgctaggt gttggagggt ttccgcccct cagtgccgca gctaacgcat      840
taagcattcc gcctgggag tacgaccgca aggttgaaac tcaaaggaat tgacgggggc       900
ccgcacaagc ggtggagcat gtggtttaat tcgaagcaac gcgaagaacc ttaccaggtc      960
ttgacatctt tgatcacct gagagatcag gtttcccctt cggggggcaaa atgacaggtg     1020
gtgcatggtt gtcgtcagct cgtgtcgtga tgttgggt taagtcccgc aacgagcgca       1080
accttatga ctagttgcca gcatttagtt gggcactcta gtaagactgc cggtgacaaa      1140
ccggaggaag gtggggatga cgtcaaatca tcatgcccct tatgacctgg gctacacacg     1200
tgctacaatg gatggtacaa cgagttgcga ccgcgagg tcaagctaat ctcttaaagc       1260
cattctcagt tcggactgta ggctgcaact cgcctacacg aagtcggaat cgctagtaat     1320
cgcggatcag cacgccgcgg tgaatacgtt cccgggcctt gtacacaccg cccgtcacac     1380
catgagagtt tgtaacaccc gaagccggtg gcgtaaccct tttagggagc gagccgtcta     1440
a                                                                     1441

<210> SEQ ID NO 2
<211> LENGTH: 1437
<212> TYPE: DNA
<213> ORGANISM: Lactobacillus rhamnosus

<400> SEQUENCE: 2
agtcgaacga gttctgatta ttgaaaggtg cttgcatctt gatttaattt tgaacgagtg       60
gcggacgggt gagtaacacg tgggtaacct gcccttaagt gggggataac atttggaaac      120
agatgctaat accgcataaa tccaagaacc gcatggttct tggctgaaag atggcgtaag      180
ctatcgcttt tggatggacc cgcggcgtat tagctagttg gtgaggtaac ggctcaccaa      240
ggcaatgata cgtagccgaa ctgagaggtt gatcggccac attgggactg agacacggcc      300
caaactccta cgggaggcag cagtagggaa tcttccacaa tggacgcaag tctgatggag      360
caacgccgcg tgagtgaaga aggctttcgg gtcgtaaaac tctgttgttg gagaagaatg      420
gtcggcagag taactgttgt cggcgtgacg gtatccaacc agaaagccac ggctaactac      480
gtgccagcag ccgcggtaat acgtaggtgg caagcgttat ccggatttat gggcgtaaa     540
gcgagcgcag gcggtttttt aagtctgatg tgaaagccct cggcttaacc gaggaagtgc      600
atcggaaact gggaaacttg agtgcagaag aggacagtgg aactccatgt gtagcggtga      660
aatgcgtaga tatatggaag aacaccagtg gcgaaggcgg ctgtctggtc tgtaactgac      720
gctgaggctc gaaagcatgg gtagcgaaca ggattagata ccctggtagt ccatgccgta      780
aacgatgaat gctaggtgtt ggagggtttc cgcccttcag tgccgcagct aacgcattaa      840
gcattccgcc tggggagtac gaccgcaagg ttgaaactca aaggaattga cgggggcccg      900
cacaagcggt ggagcatgtg gtttaattcg aagcaacgcg aagaaccttta ccaggtcttg      960
```

```
                                                     -continued acatcttttg atcacctgag agatcaggtt tccccttcgg gggcaaaatg acaggtggtg    1020
catggttgtc gtcagctcgt gtcgtgagat gttgggttaa gtcccgcaac gagcgcaacc    1080
cttatgacta gttgccagca tttagttggg cactctagta agactgccgg tgacaaaccg    1140
gaggaaggtg gggatgacgt caaatcatca tgccccttat gacctgggct acacacgtgc    1200
tacaatggat ggtacaacga gttgcgagac cgcgaggtca agctaatctc ttaaagccat    1260
tctcagttcg gactgtaggc tgcaactcgc ctacacgaag tcggaatcgc tagtaatcgc    1320
ggatcagcac gccgcggtga atacgttccc gggccttgta cacaccgccc gtcacaccat    1380
gagagtttgt aacacccgaa gccggtggcg taacccttt agggagcgag ccgtcta       1437
```

LACTOBACILLUS HAVING ANTIMICROBIAL EFFECT ON GARDNERELLA VAGINALIS AND CANDIDA ALBICANS

CROSS-REFERENCE TO RELATED APPLICATIONS

This application is based on and claims priority from Korean Patent Application No. 10-2019-0052198, filed on May 3, 2019, with the Korean Intellectual Property Office, the disclosure of which is incorporated herein in its entirety by reference.

STATEMENT REGARDING ELECTRONIC FILING OF A SEQUENCE LISTING

A Sequence Listing in ASCII text format, submitted under 37 C.F.R. § 1.821, entitled 1547-3_ST25.txt, 4,345 bytes in size, generated on Mar. 25, 2020 and filed via EFS-Web, is provided in lieu of a paper copy. This Sequence Listing is hereby incorporated by reference into the specification for its disclosures.

TECHNICAL FIELD

The present disclosure relates to a *lactobacillus* strain having antimicrobial activity against *Gardnerella vaginalis* and *Candida albicans*, a culture medium of the strain, and a cell-free supernatant of the strain, and to a antimicrobial composition containing the same, a pharmaceutical composition for preventing or treating *Gardnerella vaginalis* infection or *Candida albicans* infection containing the same, a pharmaceutical composition for prevention or treatment of vaginitis containing the same, a health functional food for prevention or ameliorating of vaginitis containing the same, and a quasi-drug composition for prevention or ameliorating of vaginitis containing the same.

BACKGROUND

*Lactobacillus* has a special biological activity, and is generally regarded as a safe bacteria. *Lactobacillus* is not only used in the production of various fermented foods but also widely used in dairy products and fermented vegetable products with functional and probiotic properties. Recently, as consumer demand for natural supplements to replace chemical supplements increases, *lactobacillus* is emerging as an alternative. Probiotics are living microorganisms that have a very beneficial effect on the host animal's health and improves the balance of intestinal microflora and promotes absorption of nutrients. Further, probiotics are characterized by the antimicrobial action of pathogenic microorganisms in the intestinal environment. Probiotics contain a variety of microorganisms. Genus *lactobacillus* and genus *bifidobacterium* have the largest content therein. In particular, the genus *lactobacillus* is commonly used in the fermentation process of dairy products, meat, vegetables and cereal products.

On the other hand, more than 90% of vaginitis in women of childbearing age is bacterial vaginosis, *Candida* vaginitis, *Trichomonas* vaginitis. The bacterial vaginosis accounts for 40 to 50% thereof. These germs do not multiply when the pH inside the woman's vagina is normal, but easily invades when the body is not normal due to overwork, stress, or taking birth control pills. This may cause complications such as postoperative infection, and complications of premature rupture of membranes and premature pain obstetrically. Thus, attention and effective treatment thereof are needed.

Women's vagina is naturally colonized with various bacteria, yeasts and microorganisms. For example, normal female vagina typically contains about $10^4$ or more *Lactobacillus* spp. per milliliter of vaginal material. Under normal conditions, the vaginal flora provides a weak acidic environment that helps protect the vagina against the invasion of pathogenic microorganism.

However, under these normal conditions, the vaginal flora, or vaginal equilibrium may be easily overturned by various external factors that ultimately lead to vaginal infection. Vaginal infections are clinical syndromes, and mainly include bacterial vaginosis, *Candida vaginitis*, and *trichomonas* vaginitis. The bacterial vaginitis is the most common.

The bacterial vaginosis is reported to be caused mainly by an increase in the number of anaerobic organisms accompanied by a decrease in *Lactobacillus* in the vagina. In addition, it is reported that the bacterial vaginosis may also be caused by bacterial or viral infections, antibiotics or contraceptives, and excessive vaginal cleansers. Reducing the number of *Lactobacillus* in the vagina reduces competition for nutrients, and will increase the pH by reducing the amount of lactic acid as present. The bacterial vaginosis is caused by the proliferation of opportunistic pathogens whose growth is usually inhibited in the vagina.

It is reported that the main pathogen associated with bacterial vaginosis caused by the proliferation of such pathogens is *Gardnerella vaginalis*. Symptoms of bacterial vaginosis caused by the infection of the *Gardnerella vaginalis* usually have an unpleasant odor from leukorrhea. Leukorrhea increases to wet underwear. The vaginal secretion discharge, that is, diluted homogeneous secretion discharge increases. pH in the vagina rises above about 5.0. Itching occurs. The presence of *Gardnerella* clue cells, which are vaginal epithelial cells coated with Gram-pathogenic bacillus occurs. The vagina is a 7 to 9 cm long tube that connects a cervix to the external genitalia. The entrance to the vagina is located between the urinary tract and the anus and acts as an excretory pathway for the secretion of substances from the cervix. The vagina of an adult woman is normally inhabited with various bacteria, including *Lactobacillus, Streptococcus* and *Staphylococcus*. The inhabitation ratio of anaerobic and aerobic bacteria is approximately 5:1. In about 20% of women, fungus *Candida* is normally found in the vagina. The type of habitat strain is affected by the glycogen and glucose content, pH, and the like of the vagina.

Normal vaginal pH is 4.5 to 5.1. The inside of the vagina is acidic because the vaginal bacteria and vaginal epithelial cells produce lactic acid using glycogen and glucose. *Lactobacillus'*, which lives in the vagina, produces lactic acid and maintains its pH, and thus plays a useful role in suppressing the growth of harmful bacteria.

Bacterial vaginitis is the most common cause of inflammation of the vagina and it is not clear whether the bacterial vaginitis is infected through sexual intercourse. However, it has been reported that bacterial vaginitis is associated with sexually transmitted diseases such as gonorrhea and *chlamydia*. Bacterial vaginitis occurs when anaerobic bacteria in the vagina are overgrown due to decreased reproduction of *Lactobacillus* among the vaginal normal bacteria. Causative strains include *Gardnerella vaginalis, Peptostreptococcus, Mobiluncus, Bacteroides*, etc. Representative symptoms include increased vaginal discharge having the color of the discharge (white or pale yellow, green, gray, etc.) and a fishy smell. The characteristic odor is due to the aromatic amine produced by the overgrown bacteria.

Vaginitis treatment methods for preventing and treating such vaginitis have been studied a lot. In recent years, vaginitis treatment agent such as metronidazole is orally administered or applied in the form of a cream for the treatment of vaginal bacterial infections. However, the use of broad spectrum antibiotics such as the metronidazole not only poses the problem of antibiotic resistance but also kills a wide range of normal bacterial flora in the vagina containing beneficial *Lactobacillus*. Thus, the use of such antibiotics is considered undesirable.

It has been reported that the death of normal vaginal flora in the vagina containing *Lactobacillus* may cause secondary complications. That is, the reduction of *Lactobacillus*, which inhibits various opportunistic pathogens in the vagina, increases the pH in the vagina, making it difficult to maintain an acidic environment, thereby accelerating the infection due to anaerobic bacteria growth, which may cause additional infection.

In addition, problems have been reported that prolonged use of antibiotics may cause systemic toxicity due to absorption of antibiotics through the vagina. Therefore, there is an urgent need to develop a safe composition for the prevention and treatment of vaginitis to inhibit and/or treat vaginal infections without side effects.

SUMMARY

The present inventors have studied probiotics as an alternative to antibiotics to prevent the occurrence and recurrence of vaginitis and to maintain women's vaginal health. Thus, among the *Lactobacillus* isolated from the vagina of Korean women, various kinds of *lactobacillus* strains with antimicrobial activity against *Gardnerella vaginalis* and *Candida albicans* were selected and characterized. Thus, we secured *lactobacillus* strains with high antimicrobial potency against *Gardnerella vaginalis* and *Candida albicans*. In this way, the present disclosure was completed.

The present disclosure has been made in an effort to provide *lactobacillus* strains with antimicrobial activity against *Gardnerella vaginalis* and *Candida albicans*, the culture medium of the strain and the cell-free supernatant of the strain.

Further, the present disclosure has been made in an effort to provide an antimicrobial composition containing the composition.

An exemplary embodiment of the present disclosure provides a *Lactobacillus paracasei* MG4272 strain with antimicrobial activity against *Gardnerella vaginalis* and *Candida albicans*.

Further, another exemplary embodiment of the present disclosure provides a composition containing one or more kinds selected from the group consisting of the strain, the culture medium of the strain and the cell-free supernatant of the strain.

Further, yet another exemplary embodiment of the present disclosure provides an antimicrobial composition containing the composition.

Further, still yet another exemplary embodiment of the present disclosure provides a pharmaceutical composition for the prevention or treatment of *Gardnerella vaginalis* infections containing the composition.

Further, still yet another exemplary embodiment of the present disclosure provides a pharmaceutical composition for the prevention or treatment of *Candida albicans* infections containing the composition.

Further, still yet another exemplary embodiment of the present disclosure provides a pharmaceutical composition for the prevention or treatment of vaginitis containing the composition.

Further, still yet another exemplary embodiment of the present disclosure a health functional food for the prevention or ameliorating of vaginitis containing the composition.

Further, still yet another exemplary embodiment of the present disclosure provides a quasi-drug composition for the prevention or ameliorating of vaginitis containing the composition.

According to the exemplary embodiments of the present disclosure, the *Lactobacillus paracasei* MG4272 strain in accordance with the present disclosure has excellent antimicrobial activity against *Gardnerella vaginalis* and *Candida albicans*, and has excellent acid resistance, bile resistance, autoaggregation ability and epithelial cell adhesion ability and is suitable for probiotics and thus may be used in various ways for the composition of prevention or treatment of *Gardnerella vaginalis* infection, *Candida albicans* infection and vaginitis.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 is a diagram showing the antimicrobial effect of 30 *lactobacillus* strains on *Gardnerella vaginalis* to select *Lactobacillus* showing a high antimicrobial effect on *Gardnerella vaginalis*.

FIG. 2 is a diagram showing the inhibitory activity of *Candida albicans* by two strains MG4272 and MG4288 having excellent antimicrobial effect against *Gardnerella vaginalis*.

FIG. 3 is a diagram showing the systematic identification of the MG4272 and MG4288 strains.

FIG. 4, panel A shows the cell morphology of the MG4272 strain, and FIG. 4, panel B shows the cell morphology of the MG4288 strain strains.

FIG. 5 is a diagram showing the inhibitory effect of the MG4272 strain against *Gardnerella vaginalis* compared with other *Lactobacillus paracasei* bacteria.

FIG. 6 is a diagram showing the inhibitory effect of MG4288 strain against *Gardnerella vaginalis* compared with other *Lactobacillus rhamnosus* bacteria.

FIG. 7 is a diagram showing the autoaggregation ability of the MG4272 and MG4288 strains.

FIG. 8 is a diagram showing xylene adhesion ability, chloroform adhesion ability, and ethyl acetate adhesion ability of MG4272 and MG4288 strains.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented herein.

The present disclosure provides *Lactobacillus paracasei* MG4272 strain with antimicrobial activity against *Gardnerella vaginalis* and *Candida albicans*.

The *Lactobacillus paracasei* MG4272 strain in accordance with the present disclosure has an excellent antimicrobial effect against *Gardnerella vaginalis* and/or *Candida albicans*, and has excellent acid resistance, bile resistance, autoaggregation, and intestinal cell adhesion ability.

Hereinafter, the present disclosure will be described in detail.

The *Lactobacillus paracasei* MG4272 strain is a strain with antimicrobial activity against *Gardnerella vaginalis* and *Candida albicans*.

In the present disclosure, the term "*Lactobacillus*" refers to a bacterium which forms a large amount of lactic acid by fermenting sugars widely distributed in nature to obtain energy and is gram-positive asporogenic bacillus morphologically and exhibits polymorphism. The *Lactobacillus paracasei* MG4272 strain has excellent antimicrobial effects on *Gardnerella vaginalis* and/or *Candida albicans* according to the present disclosure and being excellent in acid resistance, bile resistance, autoaggregation and epithelial cell adhesion ability. The *Lactobacillus paracasei* MG4272 strain was deposited on Mar. 12, 2019 in the Korea Research Institute of Bioscience and Biotechnology, Korean Collection for Type Cultures (KC717C): 181 Ipsin-gil, Jeongeup-si, Jeollabuk-do 56212, Korea, which is an international depository authority under the Budapest Treaty and was assigned accession number KCTC13822BP. The present inventors identified the *Lactobacillus paracasei* MG4272 strain as follows.

To isolate the *lactobacillus* strain according to the present disclosure, we isolated the strain from the vagina of healthy Korean women. There are numerous *lactobacillus* strains in healthy vagina and their distribution varies according to race, age and environment. Among the isolated strains, two strains with the highest activity against *Gardnerella vaginalis* were selected and identified. Thus, the two strains were *Lactobacillus paracasei* MG4272 and *Lactobacillus rhamnosus* MG4288.

The *Lactobacillus paracasei* MG4272 strain in accordance with the present disclosure has excellent antimicrobial effects against *Gardnerella vaginalis* and/or *Candida albicans*.

The strain in accordance with the present disclosure is morphologically bacillus.

The strain in accordance with the present disclosure may be acid resistant and may be preferably stable at pH 3 to pH 7, and may be more preferably stable at pH 3 to pH 4 as the gastric fluid condition in the body containing pepsin.

The strain may have bile resistance. Preferably, the strain may be stable under the conditions of pH 7 to pH 9. More preferably, the strain may be stable under the treatment conditions of the bile salts containing pancreatin or pH 7 to pH 8.

The *Lactobacillus paracasei* MG4272 strain in accordance with the present disclosure has an excellent autoaggregation ability and has high cell surface hydrophobicity, resulting in high epithelial cell adhesion ability. Therefore, the *Lactobacillus paracasei* MG4272 strain in accordance with the present disclosure may prevent the removal of probiotics by intestinal spasms and form colony on epithelial cells effectively in the intestine or vagina, thus and may settle well in the intestine or vagina. This cell adhesion ability is effective in maintaining the effect of probiotics for vaginal health.

The *Lactobacillus paracasei* MG4272 strain in accordance with the present disclosure may be antibiotic resistant to cefotaxime, cefotetan, kanamycin, streptomycin, nalidixic acid, trimethoprim-sulphamethoxazole, and vancomycin, and may have antibiotic susceptibility to ampicillin, ciprofloxacin, tetracycline, erythromycin and rifampin.

The *Lactobacillus paracasei* MG4272 strain in accordance with the present disclosure may have sugar fermentation properties for D-ribose, D-galactose, D-glucose, D-fructose, D-mannose, L-sorbose, D-mannitol, D-sorbitol, N-acetyl-glucosamine, Amygdalin, Arbutin, Esculin, Salicin, D-cellobiose, D-maltose, D-sucrose, Inulin, D-melezitose, Gentiobiose, D-turanose, D-tagatose, L-ararabirol and gluconate.

The *Lactobacillus paracasei* MG4272 strain in accordance with the present disclosure may exhibit enzymatic activity on Esterase (C4), Esterase lipase (C8), Leucine arylamidase, Valine arylamidase, Acid phosphatase, Naphtol-AS-BI-phosphohydrolase, β-glucuronidase, α-glucosidase, and β-glucosidase.

Cell surface hydrophobicity means the presence of proteins on the cell surface. Cell surface hydrophilicity means that there are many polysaccharides on the cell surface. The more protein on the cell surface, the better the autoaggregation ability and cell adhesion ability. The *Lactobacillus paracasei* MG4272 strain in accordance with the present disclosure has high xylene adhesion ability, which may render the surface of the cell hydrophobic. Autoaggregation ability and cell adhesion ability thereof may be excellent.

Further, the present disclosure provides a composition containing one or more kinds selected from the group consisting of the strain, the culture medium of the strain and the cell-free supernatant of the strain.

Further, the present disclosure provides an antimicrobial composition containing the composition.

In the present disclosure, the antimicrobial composition may be synonymous with antibiotics, which collectively means antimicrobial agents may mean an antifungal, fungicide, preservative, preserved agent or fungistat. Preferably, the antimicrobial composition may be a substance capable of suppressing or inhibiting the development and life functions of pathogenic microorganisms causing vaginitis. More preferably, the antimicrobial composition may be a substance capable of suppressing or inhibiting the development and life function of *Gardnerella vaginalis* or *Candida albicans*. However, the present disclosure is not limited thereto.

Further, the present disclosure provides a pharmaceutical composition for the prevention or treatment of *Gardnerella vaginalis* infections containing the composition.

Further, the present disclosure provides a pharmaceutical composition for the prevention or treatment of *Candida albicans* infections containing the composition.

Further, the present disclosure provides a pharmaceutical composition for the prevention or treatment of vaginitis containing the composition.

In the present disclosure, the term "prevention" means any action that inhibits or delays the development of *Gardnerella vaginalis* infection, *Candida albicans* infection, or vaginitis via the administration of a pharmaceutical composition for the prevention or treatment of *Gardnerella vaginalis* infection, *Candida albicans* infection or vaginitis according to the present disclosure.

In the present disclosure, the term "treatment" means any action that reduces or benefits the symptoms of *Gardnerella vaginalis* infection, *Candida albicans* infection, or vaginitis via administering of a composition according to the present disclosure to an individual suspected of developing *Gardnerella vaginalis* infection, *Candida albicans* infection, or vaginitis.

*Gardnerella vaginalis* infection of the present disclosure may be a disease caused by *Gardnerella vaginalis* infection, preferably bacterial vaginosis by *Gardnerella vaginalis*.

*Candida albicans* infection of the present disclosure may be caused by *Candida albicans* infection, and, preferably may be vaginal candidiasis caused by *Candida albicans*.

In the present disclosure, the term "vaginitis" may be one or more diseases selected from the group containing bacterial vaginosis, vaginal candidiasis, trichomoniasis and atrophic vaginitis. Preferably, the vaginitis may be bacterial vaginosis due to vaginal candidiasis or *Gardnerella vaginalis* infection due to *Candida albicans* infection.

The pharmaceutical composition for the prevention or treatment of *Gardnerella vaginalis* infection, *Candida albicans* infection or vaginitis in accordance with the present disclosure may be applied directly to animals containing humans. The animal is a biome that corresponds to plants, and consumes mainly organic matter and has digestion or excretion and respiratory organs as differentiated. Preferably, the animal may be a vertebrate, more preferably a mammal. The mammal may preferably be a human.

The pharmaceutical composition for the prevention or treatment of the *Gardnerella vaginalis* infection, *Candida albicans* infection or vaginitis may contain the strain, strain culture medium or cell-free supernatant alone as an active ingredient. In addition, depending on the formulation, method of use and purpose of use thereof, the composition may further contain additional ingredients, that is, pharmaceutically acceptable or nutritionally acceptable carriers, excipients, diluents or accessory ingredients.

More specifically, the composition for the prevention or treatment of the *Gardnerella vaginalis* infection, *Candida albicans* infection or vaginitis may contain, in addition to the active ingredient, nutritional supplements, vitamins, electrolytes, flavors, coloring agents, enhancers, pectic acid and salts thereof, alginic acid and its salt, organic acids, protective colloidal thickeners, pH adjusters, stabilizers, preservatives, glycerin, alcohols, carbonation agents used in carbonated beverages, and the like.

Further, the carrier, excipient or diluent may be at least one kind selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil, dextrin, calcium carbonate, propylene glycol, liquid paraffin, and physiological saline, but may not limited to thereto. All of conventional carriers, excipients or diluents are available. The ingredients may be added independently or in combination with each other to the pharmaceutical composition as the active ingredient.

Further, when the pharmaceutical composition for the prevention or treatment of the *Gardnerella vaginalis* infection, *Candida albicans* infection or vaginitis is formulated, the composition may further contain conventional fillers, extenders, binders, disintegrant, surfactant, anti-coagulant, lubricant, wetting agent, fragrance, emulsifier or preservative. For example, the composition may be used orally or parenterally.

The dosage of the pharmaceutical composition for preventing or treating *Gardnerella vaginalis* infection, *Candida albicans* infection or vaginitis according to the present disclosure may be selected appropriately by the skilled person to the art in consideration of the method of administration, the age, sex and weight of the recipient, and the severity of the disease. For example, the pharmaceutical composition for preventing or treating *Gardnerella vaginalis* infection, *Candida albicans* infection or vaginitis of the present disclosure may be administered at 0.0001 mg/kg to 1,000 mg/kg, 0.01 mg/kg to 100 mg/kg in a more effective manner Administration may be done once a day or the composition may be administered several times. The dosage does not in any way limit the scope of the present disclosure.

Further, the pharmaceutical composition for the prevention or treatment of *Gardnerella vaginalis* infection, *Candida albicans* infection or vaginitis in accordance with the present disclosure may further contain a known compound or plant extract having a *Gardnerella vaginalis* infection, *Candida albicans* infection or vaginitis inhibitory activity in addition to the composition. The known compound or plant extract may be contained in 5 parts by weight to 20 parts by weight, based on 100 parts by weight of the pharmaceutical composition.

Further, the present disclosure provides a health functional food composition for the prevention or ameliorating of vaginitis containing the composition.

The health functional food to which the composition in accordance with the present disclosure may be added may include, for example, various foods, beverages, gums, candies, teas, vitamin complexes, functional foods, and the like. In addition, in the present disclosure, the food includes special nutritional products (e.g., milk formulas, infant food, baby food, etc.), processed meats, fish products, tofu, jelly, noodles (e.g. ramen, noodles, etc.), health supplements, seasoned foods (e.g. soy sauce, miso, red pepper paste, mixed soy sauce, etc.), sauces, confectionery (e.g. snacks), dairy products (e.g. fermented milk, cheese, etc.), other processed foods, kimchi, pickles (various kimchi, pickled vegetables, etc.), beverages (e.g. fruits, vegetable drinks, soy milk, fermented beverages, ice cream, etc.), natural seasonings (e.g. ramen soup, etc.), vitamin complexes, alcoholic beverages, alcohol, and other health supplement foods, but may not be limited thereto. The food, beverage or food additive may be prepared using conventional preparation methods.

In the present disclosure, the health functional food means a group of foods which is processed using physical, biochemical, or biotechnological techniques to function and express the function of the corresponding food for a specific purpose or means foods that are designed and processed to fully express body regulation functions such as biodefense rhythm control, disease prevention and recovery, etc., on the body. Preferably, the health functional food of the present disclosure means a food capable of sufficiently expressing a bioregulatory function on a living body for preventing or improving vaginitis. The health functional food may contain cytologically acceptable food supplements, and may further contain appropriate carriers, excipients and diluents commonly used in the preparation of the health functional food.

Further, the present disclosure provides a quasi-drug composition for the prevention or ameliorating of vaginitis containing the composition.

When the *Lactobacillus paracasei* MG4272 strain in accordance with the present disclosure is used as a quasi-drug composition, the strain, the strain culture medium or the cell-free supernatant of the strain may be added thereto as it is or may be used together with other quasi-drug components and may be suitably used according to a conventional method. A mixed amount of the active ingredient may be appropriately determined depending on the purpose of use (prevention, health or therapeutic treatment).

Preferably, the quasi-drug composition may be a disinfectant cleaner, a shower foam, garglin, a wet tissue, a detergent soap, a hand wash, a humidifier filler, a mask, an ointment, or a filter filler.

The *Lactobacillus paracasei* MG4272 strain and *Lactobacillus rhamnosus* MG4288 strain in accordance with the present disclosure have similar properties and may be used in combination with each other for better antimicrobial activity. When the two strains are used in combination with each other, an unexpected and more significant effect may be achieved than the antimicrobial effect achieved in using each strain alone.

Further, the present disclosure provides a method of treating an animal having a *Gardnerella vaginalis* infection comprising administering an effective amount of the composition containing one or more kinds selected from the group consisting of the strain, the culture medium of the strain and the cell-free supernatant of the strain.

Further, the present disclosure provides a method of treating an animal having a *Candida albicans* infection comprising administering an effective amount of the composition containing one or more kinds selected from the group consisting of the strain, the culture medium of the strain and the cell-free supernatant of the strain.

Further, the present disclosure provides a method of treating an animal having a vaginitis comprising administering an effective amount of the composition containing one or more kinds selected from the group consisting of the strain, the culture medium of the strain and the cell-free supernatant of the strain.

As used herein, the term "animal" including a human, who has or is likely to develop a *Gardnerella vaginalis* infection related disease, a *Candida albicans* infection related disease or a vaginitis.

The composition may contain the strain, strain culture medium or cell-free supernatant alone as an active ingredient. In addition, depending on the formulation, method of use and purpose of use thereof, the composition may further contain additional ingredients, that is, pharmaceutically acceptable or nutritionally acceptable carriers, excipients, diluents or accessory ingredients.

More specifically, the composition may contain, in addition to the active ingredient, nutritional supplements, vitamins, electrolytes, flavors, coloring agents, enhancers, pectic acid and salts thereof, alginic acid and its salt, organic acids, protective colloidal thickeners, pH adjusters, stabilizers, preservatives, glycerin, alcohols, carbonation agents used in carbonated beverages, and the like.

Further, the carrier, excipient or diluent may be at least one kind selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil, dextrin, calcium carbonate, propylene glycol, liquid paraffin, and physiological saline, but may not limited to thereto. All of conventional carriers, excipients or diluents are available. The ingredients may be added independently or in combination with each other to the pharmaceutical composition as the active ingredient.

Further, when the composition is formulated, the composition may further contain conventional fillers, extenders, binders, disintegrant, surfactant, anti-coagulant, lubricant, wetting agent, fragrance, emulsifier or preservative. For example, the composition may be used orally or parenterally.

The dosage of the composition may be selected appropriately by the skilled person to the art in consideration of the method of administration, the age, sex and weight of the recipient, and the severity of the disease. For example, the composition of the present disclosure may be administered at 0.0001 mg/kg to 1,000 mg/kg, 0.01 mg/kg to 100 mg/kg in a more effective manner. Administration may be done once a day or the composition may be administered several times. The dosage does not in any way limit the scope of the present disclosure.

Further, the composition in accordance with the present disclosure may further contain a known compound or plant extract having a *Gardnerella vaginalis* infection, *Candida albicans* infection or vaginitis inhibitory activity in addition to the composition. The known compound or plant extract may be contained in 5 parts by weight to 20 parts by weight, based on 100 parts by weight of the composition.

Duplicate content is omitted in consideration of the complexity of the present specification. Terms not otherwise defined herein have a meaning commonly used in the art to which the present disclosure belongs.

Hereinafter, the present disclosure will be described in detail with Examples. However, the following Example merely illustrates the present disclosure, and the content of the present disclosure is not limited by the following Example.

Example 1. Selection of *Lactobacillus* with Antimicrobial Effect on *Gardnerella vaginalis*

Among the 30 strains of *Lactobacillus* isolated from the vagina of healthy Korean women who had never developed vaginitis within 6 months and involved in a joint study with the Department of Obstetrics and Gynecology, Ewha Womans University Medical Center, *Lactobacillus* which has an antimicrobial effect against *Gardnerella vaginalis* (KCTC5096, *G. vaginalis*), as a major causative agent of bacterial vaginosis was selected by dilution with liquid medium. Culture of *Gardnerella vaginalis* was performed using BHI medium (Difco, MI, USA) containing 10% horse serum (Horse serum, Life technologies corp., NY, USA) (hereinafter, mBHI) and at 37° C. for 24 hours while an anaerobic condition was maintained using Anaerocult® A (Merck, Germany). A single colonies grown on MRS plate medium (Difco, MI, USA) were inoculated into MRS liquid medium. Lactobacilli's strains was cultured at 37° C. for 24 hours in a stationary manner. Then, the absorbance of the culture medium was adjusted to $OD_{600}$ 1.0 ($10^8$ to $10^9$ CFU/mL) and the culture medium was inoculated into 1% of fresh MRS liquid medium. The culture medium incubated at 37° C. for 18 hours in a stationary manner was filtered using a 0.22 µL filter, and the filtered supernatant (cell free supernatant (CFS)) was used in this experiment. As a control, MRS liquid medium not inoculated with *lactobacillus* strain was treated in the above same manner. To identify the antimicrobial effect on *Gardnerella vaginalis*, 0.5 mL of CFS of each *lactobacillus* strain was added to 4.5 mL mBHI medium and then the culture medium of *Gardnerella vaginalis* was adjusted to OD6000.5 and was inoculated thereto by 1%. After 24 hours of anaerobic culture, viable cell counts of *Gardnerella vaginalis* were identified and the antimicrobial effect of each *lactobacillus* strain was identified. The result was shown in FIG. 1.

As shown in FIG. 1, 19 strains of *Lactobacillus* exhibited antimicrobial effects against *Gardnerella vaginalis* compared to the control. Among 19 strains, MG4272 and MG4288 strains showed 61.36% and 79.60% inhibition rate, respectively compared to the control and thus exhibited high antimicrobial effect compared to other isolated strains.

Example 2. Antifungal Effect of MG4272 and MG4288 Strains on *Candida albicans*

Antifungal effects of MG4272 and MG4288 as *lactobacillus* strains selected based on antifungal effects against *Gardnerella vaginalis* against *Candida albicans* SC5314 (*C. albicans*) as a major causative agent of *Candida* vaginitis were identified. MG4272 and MG4288 strains were cultured with MRS liquid medium and *Candida albicans* was cultured with YM (0.3% malt extract, 0.3% yeast extract, 0.5% peptone, 1% glucose) liquid medium at 37° C. for 18 hours. *Lactobacillus* strains and *Candida albicans* strains were inoculated in 10 mL of a mixed medium of the MRS liquid medium and YM liquid medium in the ratio of 1:1 to reach a final concentration of $10^5$ CFU/mL, and then were incubated at 37° C. for 20 hours in a stationary manner. After the incubation, the viable cell count of *Candida albicans* was measured using YM solid plate medium coated with erythromycin (0.3 μL/mL). For the cell-free supernatants of the MG4272 and MG4288 strains as prepared in Example 1, the antifungal effect test against *Candida albicans* was performed in the same way. Then, the viable cell count of *Candida albicans* was measured. The results are shown in FIG. 2.

As shown in FIG. 2, two strains MG4272 and MG4288, which have superior antimicrobial activity against *Gardnerella vaginalis*, exhibited inhibitory activity on *Candida albicans*. In the mixing culture of *Candida albicans* and *Lactobacillus*, MG4272 inhibited the growth of *Candida albicans* by 91.4%. MG4288 inhibited the growth of *Candida albicans* by 97.3%. Regarding the antifungal effect on the cell-free supernatant of *lactobacillus* strains, MG4272 inhibited the growth of *Candida albicans* by 97.4% and MG4288 inhibited the growth of *Candida albicans* by 97.6%. The MG4288 strain was similar to the mixing culture in terms of the inhibition of the CFS. Thus, it was identified that the mixing culture maintained the inhibition rate without being inhibited by *Candida albicans*.

Example 3. Identification of MG4272 and MG4288 Strains 3.1 Sequence Analysis and Phylogenetic Tree Identification of MG4272 and MG4288 Strains 16S rRNA gene sequencing was performed using universal rRNA gene primers (27F, 1492R) of MG4272 and MG4288 strains. Each process was performed through Solgent (Daejeon, Korea). The analyzed sequences were compared and identified with the Genebank database using the Basic Local Alignment Search Tool (Blast) of the National Center for Biotechnology Institute (NCBI). The phylogenetic tree was created using the neighbor joining method of MEGA 7.0 software. The 16s rRNA sequence of the analyzed MG4272 strain was shown as SEQ ID NO: 1, and 16s rRNA base sequence of the MG4288 strain was shown in SEQ ID NO: 2. The phylogenetic tree of the MG4272 and MG4288 strains was shown in FIG. 3.

As shown in FIG. 3, the two strains with superior antimicrobial activity against *Gardnerella vaginalis* and *Candida albicans* were identified to be *Lactobacillus paracasei* MG4272 and *Lactobacillus rhamnosus* MG4288 based on the 16S rRNA sequences analysis. The identified *Lactobacillus paracasei* MG4272 was deposited on Mar. 12, 2019 on the Korean Collection for Type Culture (Korea) and was assigned accession number KCTC13822BP. *Lactobacillus rhamnosus* MG4288 was deposited on Mar. 12, 2019 on the Korean Collection for Type Culture (Korea) and was assigned accession number KCTC13823BP.

3.2 Identification of Morphological Characteristics of MG4272 and MG4288 Strains To identify the morphological characteristics of MG4272 and MG4288 strains, the MG4272 and MG4288 strains were immobilized in 1% glutaraldehyde (Sigma-Aldrich, Saint Louise, USA) solution at 4° C. for 24 hours, and were dehydrated with ethanol and observed using a scanning electron microscope (Field emission scanning electron microscope, 54300, Hitach, Tokyo, Japan). The observed results are shown in FIG. 4.

As shown in FIG. 4, the cell morphology of the MG4272 and MG4288 strains was identified to be bacillus by the scanning electron microscope.

The MG4272 and MG4288 strains selected in accordance with the present disclosure were *Lactobacillus paracasei* or *Lactobacillus rhamnosus* strains, respectively. Both *Lactobacillus paracasei* and *Lactobacillus rhamnosus* strains are listed in the standards and specifications of the Ministry of Food and Drug Safety and functional foods and are safe.

Example 4. Comparison of Antimicrobial Effects Against *Gardnerella vaginalis* by *Lactobacillus paracasei* Strain and *Lactobacillus paracasei* MG4272 Strain and by Strains Belonging to Same Species 4.1 Comparison of Antimicrobial Effects Against *Gardnerella vaginalis* by Other *Lactobacillus paracasei* Strains and by *Lactobacillus paracasei* MG4272 Strain To compare the antimicrobial effects against *Gardnerella vaginalis* between *Lactobacillus paracasei* MG4247 strains and other *Lactobacillus paracasei* strains, the same experiment as in Example 1 was performed twice on *Lactobacillus paracasei* MG4272, *Lactobacillus paracasei* MG5009, *Lactobacillus paracasei* MG5010, and *Lactobacillus paracasei* MG5012 strain. The results are shown in FIG. 5.

As shown in FIG. 5, the average *Gardnerella vaginalis* inhibitory effect of the *Lactobacillus paracasei* MG4272 strain was identified as 66.67%. The inhibitory effect on *Gardnerella vaginalis* thereof was superior to those of other *Lactobacillus paracasei* strains.

4.2 Comparison of the Antimicrobial Effects Against *Gardnerella vaginalis* Between Other *Lactobacillus rhamnosus* Strains and *Lactobacillus rhamnosus* MG4288 Strain To compare the antimicrobial effects on *Gardnerella vaginalis* between *Lactobacillus rhamnosus* MG4288 strain and other *Lactobacillus rhamnosus* strains, the same experiment as in Example 1 was performed twice on *Lactobacillus rhamnosus* MG4288, *Lactobacillus rhamnosus* MG4283, *Lactobacillus rhamnosus* MG4289, *Lactobacillus rhamnosus* MG4298 strain, and *Lactobacillus rhamnosus* MG5007 strain. The results are shown in FIG. 6.

As shown in FIG. 6, the average inhibitory effect against *Gardnerella vaginalis* by the *Lactobacillus rhamnosus* MG4288 strain was 79.61%. The inhibitory effect thereof on *Gardnerella vaginalis* was superior to those of other *Lactobacillus rhamnosus* strains.

Example 5. Identification of Resistance to Artificial Gastric Juice and Bile Juice of MG4272 and MG4288 Strains The *Lactobacillus* ingested through the oral cavity passes through the stomach with the lower acidity and the intestines with high digestive enzymes and are exposed to low pH of gastric acid, pepsin, intestinal bile salts and digestive enzymes. Therefore, in order to utilize microorganisms as probiotics, gastric juice resistance is essential to survive in low pH and enzymes, and bile juice resistance is essential to survive in extreme intestinal environment. In accordance with the present disclosure, experiments were conducted to identify resistance to artificial gastric juice and bile juice of the above two strains with superior inhibitory effects against *Gardnerella vaginalis* and *Candida albicans*. The pH of the gastric juice in the body is maintained at about 3.0, and the food passes through the stomach for about 3 hours. In general, when maintaining viable cell count for 3 hours or more at pH 3, the cells has the high resistance to acidity. In order to identify the intestinal viability of *Lactobacillus*, survival experiments for artificial gastric juice and artificial bile juice were conducted with reference to Maragkoudakis' method. MG4272 and MG4288 strains were streaked on MRS plate medium and incubated at 37° C. for 24 hours, and the resulting colonies were inoculated in MRS liquid medium and incubated (37° C., 24 hours). Then, 2% passage was incubated for 24 hours in fresh MRS medium. The culture medium was then centrifuged (4,000×g, 4° C., 5 minutes) and washed twice with phosphate-buffer saline (PBS, pH 7.4). The washed cells were adjusted to $OD_{600}$ 1.0 ($10^8$ to $10^9$ CFU/mL) and used for resistance experiments to the artificial gastric juice and artificial bile solution, respectively. As a control, 900 μL of pH 7 PBS was added to 100 μL of diluted *Lactobacillus* and the mixture was shaken and the number of viable cells was measured immediately. In order to identify the resistance to gastric juice, pepsin (Sigma-Aldrich, Saint Louise, USA) was dissolved in 3 g/L of pH 3 to pH 4 PBS to prepare an artificial gastric juice. 100 μL of *lactobacillus* diluent was added to 900 μL of artificial gastric juice, shaken, and cultured at 37° C. In 3 hours, the viable cell count was measured. To identify resistance to the artificial bile juice, pancreatin (Sigma-Aldrich, Saint Louise, USA) was dissolved in 1 g/L at pH 7 to pH 8 to prepare artificial bile juice. 100 μL of *lactobacillus diluent was added to* 900 μL of artificial bile juice, shaken and incubated at 37° C. In 4 hours, the viable cell count was measured. The measured results are shown in Table 1 in terms of log CFU/ml.

TABLE 1

| Selected strains | Control | Artificial gastric juice test group | | Artificial bile solution test group | |
|---|---|---|---|---|---|
| | | pH 3 | pH 4 | pH 7 | pH 8 |
| MG4272 | 8.53 ± 0.01 | 8.47 ± 0.01 | 8.52 ± 0.01 | 8.52 ± 0.02 | 8.49 ± 0.02 |
| MG4288 | 8.46 ± 0.06 | 8.40 ± 0.04 | 8.44 ± 0.02 | 8.41 ± 0.01 | 8.41 ± 0.02 |

As shown in Table 1 both strains of MG4272 and MG4288 were identified to maintain the viable cell count of $10^8$ CFU/mL or more after 3 hours at pH 3, thereby identifying excellent acid resistance. In the artificial bile resistance test, both strains of MG4272 and MG4288 were identified to maintain the viable cell count of $10^8$ CFU/mL or more, thereby identifying excellent bile resistance.

Example 6. Identification of Autoaggregation and Hydrophobicity of MG4272 and MG4288 Strains Autoaggregation and hydrophobicity are indirect factors for identifying the epithelial cell adhesion ability of microorganisms. According to Kos' research, strains with high autoaggregation ability and high cell surface hydrophobicity have high cell adhesion ability. When the cell adhesion ability of the microorganisms is reduced, the microorganisms are washed away because they cannot settle in the vagina due to menstruation or childbirth. Thus, cell adhesion ability is very important in probiotics for vaginal health.

6.1 Autoaggregation Identification of MG4272 and MG4288 Strains

In order to indirectly identify intestinal cell adhesion ability, Kassa's study was modified and autoaggregation experiment was conducted. *Lactobacillus* culture medium incubated in MRS medium for 18 hours was inoculated at 2% in fresh 10 mL MRS medium, and then cultured for 18 hours and used for the experiment. The cultured *Lactobacillus* was centrifuged (4,000×g, 4° C., 5 minutes), and then washed twice in PBS. Cells were adjusted to $OD_{600}$ 1.0. 5 mL of the strain suspension was shaken for 10 seconds. Then, immediately after the start of the experiment (A0) and 5 hours after the suspension was left (A), 0.1 mL of supernatant was taken and mixed with 0.9 mL of PBS. Then, absorbance thereof was measured at 600 nm. The autoaggregation ratio was calculated according to the following formula. The results are shown in FIG. 7.

$$\text{Autoaggregation}(\%) = \frac{(A0 - A)}{A0} \times 100$$

As shown in FIG. 7, autoaggregation abilities for MG4272 and MG4288 strains were 57.99% and 65.65%, respectively. According to Malik's study, when the in vitro autoaggregation of *L. plantarum* CMPG5300 was about 67%, the adhesion ability on the vaginal epithelial cells was 50% or more. Strains with high autoaggregation ability showed excellent ability to form a biofilm on the cell surface. The autoaggregation capability of MG4272 and MG4288 strains was identified to be excellent when considering that the autoaggregation capability of 8 strains except *L. plantarum* CMPG5300 was 20% or lower.

6.2 Identification of Hydrophobicity of MG4272 and MG4288 Strains

To indirectly identify intestinal cell adhesion ability, hydrophobicity was identified by modifying the microbial adhesion to KOS solvents (MATS) test method. The selected strain was incubated in MRS medium (37° C., 24 hours), followed by centrifugation (4,000×g, 4° C., 5 minutes) and washing twice in PBS. The cells were suspended to $OD_{690}$ 1.0 (A0) using PBS, and 2 mL of suspension was dispensed in 2 mL of xylene, chloroform, and ethylacetate. Each test tube was shaken for 5 minutes and left at room temperature for 30 minutes. After recovering the aqueous solution, the absorbance thereof was measured at 600 nm (A). Solvent adhesion ability was calculated according to the following formula. The results are shown in FIG. 8.

$$\text{Adhesion rate (\%)} = \frac{(A0 - A)}{A0} \times 100$$

As shown in FIG. 8, the xylene adhesion ability showing the hydrophobicity of the cells showed high hydrophobicity of 71.20% for the MG4272 strain and 83.56% for the MG4288 strain. Cell surface hydrophobicity means the presence of proteins on the cell surface. The hydrophilic property means that there are many polysaccharides. The more proteins, the better the autoaggregation ability and the cell adhesion ability. Strains with excellent cell adhesion ability have the properties to settle on the cells to inhibit cell adhesion of pathogens to prevent infection thereof. The selected two strains were identified as having high autoaggregation ability and xylene adhesion ability and thus having high epithelial cell adhesion ability and thus were attached to the inner face of the vagina to prevent further pathogen infection.

Further, as shown in FIG. 8, from a result of identifying chloroform and ethyl acetate adhesion ability to identify cell surface properties, it was confirmed that both of the MG4272 and MG4288 strains showed higher adhesion ability to acidic solvent chloroform (electron acceptor). Thus, the MG4272 and MG4288 strains were identified as receiving the electron donor on the cell surface.

Example 7. Antibiotic Susceptibility Testing of MG4272 and MG4288 Strains

Antibiotic susceptibility experiments of MG4272 and MG4288 strains were performed using Brain Heart Infusion Agar (BHI) plate medium according to the Clinical and Laboratory Standard Institute (CLSI) guidelines. The selected strains were inoculated in 1% in MRS medium, and cultured for 18 hours. The culture medium was centrifuged (4,000×g, 4° C., 5 minutes) and washed twice in PBS. After adjusting the turbidity of the strain solution to McFarland turbidity standard 0.5, the strain was plated on the BHI plate medium using a sterile cotton swab. After the medium was dried, the antibiotic disk was placed on the medium on which the bacterial solution was smeared and then the strain was incubated at 37° C. for 24 hours. The size of the produced inhibitory ring was measured in mm, and the susceptibility level was determined in three stages of sensitive, intermediate, and resistant according to standard indicators. The test for the antibiotics was executed for ampicillin (AM, 10 μg), cefotaxime (CTX, 30 μg), cefepime (CEP, 30 μg), cefotetan (CTT, 30 μg), cephalothin (CF, 30 μg), gentamicin (GM, 10 μg), kanamycin (K, 30 μg), streptomycin (S, 10 μg), ciprofloxacin (CIP, 5 μg), nalidixic acid (NA, 30 μg), trimethoprim-sulphamethoxazole (SXT, 1.25/23.75 μg), rifampin (RA, 5 μg), tetracycline (TE, 30 μg), erythromycin (E, 15 μg), and vancomycin (VA, 30 μg). The result was shown in Table 2.

TABLE 2

| | selected strains | |
|---|---|---|
| Antibiotics (μg/disc) | L. paracasei MG4272 | L. rhamnosus MG4288 |
| Ampicillin (AM, 10) | S[1] | S |
| Cefotaxime (CTX, 30) | R[2] | R |
| Cefepime (CEP, 30) | S | R |
| Cefotetan (CTT, 30) | R | R |
| Cephalothin (CF, 30) | S | R |
| Gentamicin (GM, 10) | S | R |
| Kanamycin (K, 30) | R | R |
| Streptomycin (S, 10) | R | R |
| Ciprofloxacin (CIP, 5) | S | S |
| Nalidixic acid (NA, 30) | R | R |
| Trimethorim-Sulphamethoxazole (SXT, 1.25/23.75) | R | R |
| Tetracyclin (TE, 30) | S | S |
| Erythromycin (E, 15) | S | S |
| Vancomycin (VA, 30) | R | R |
| Rifampin (RA, 5) | S | S |

[1]Sensitive,
[2]Resistant

As shown in Table 2, both strains MG4272 and MG4288 were identified to be resistant to CTX, CTT, K, S, NA, SXT, and VA and were identified as having antibiotic susceptibility to AM, CIP, TE, E, and RA.

Example 8. Identification of API Sugar Fermentation Characteristics of MG4272 and MG4288 Strains After MG4272 strain or MG4288 strain was streaked on an MRS plate medium and incubated at 37° C. for 24 hours, the resulting colonies were inoculated in MRS liquid medium for stationary culture (37° C., 24 hours). Subsequently, 2% passage in fresh MRS medium was subjected to 24 hours incubation in a stationary manner. The culture medium was then centrifuged (4,000×g, 4° C., 5 minutes) and washed twice with phosphate-buffered saline (phosphate-buffer saline, PBS, pH 7.4). After adjusting the turbidity of the washed cells to 2 McFarland using 10 mL API 50 CHL medium (BioMérieux, France), the washed cells were used for the test. The API 50 CHL medium having the bacteria suspended therein was dispensed into the tube of the strip and mineral oil was added thereto to bring the tube to an anaerobic state. After incubation thereof at 37° C. for 48 hours, the results were identified. The results of Lactobacillus paracasei MG4272 are shown in Table 3. Table 4 shows the results for Lactobacillus rhamnosus MG4288.

TABLE 3

| Substrate | MG4272 |
|---|---|
| Control (Negative) | − |
| Glycerol | − |
| Erythritol | − |
| D-arabinose | − |
| L-arabinose | − |
| D-ribose | + |
| D-xylose | − |
| L-xylose | − |
| D-adonitol | − |
| Methyl-β-D-xylopyranoside | − |
| D-galactose | + |
| D-glucose | + |
| D-fructose | + |
| D-mannose | + |

TABLE 3-continued

| Substrate | MG4272 |
|---|---|
| L-sorbose | + |
| L-rhamnose | − |
| Dulcitol | − |
| Inositol | − |
| D-mannitol | + |
| D-sorbitol | + |
| Methyl-α D-Mannoside | − |
| Methyl-α D-glucoside | − |
| N-acethyl-glucosamine | + |
| Amygdalin | + |
| Arbutin | + |
| Esculin | + |
| Salicin | + |
| D-cellobiose | + |
| D-maltose | + |
| D-lactose | − |
| D-melibiose | − |
| D-sucrose | + |
| D-trehalose | − |
| Inulin | + |
| D-melezitose | + |
| D-raffinose | − |
| Starch | − |
| Glycogen | − |
| Xylitol | − |
| Gentiobiose | + |
| D-turanose | + |
| D-lyxose | − |
| D-tagatose | + |
| D-fucose | − |
| L-fucose | − |
| D-arabitol | − |
| L-arabirol | + |
| Gluconate | + |
| 2-keto-gluconate | − |
| 5-keto-gluconate | − |

TABLE 4

| Substrate | MG4288 |
|---|---|
| Control (Negative) | − |
| Glycerol | − |
| Erythritol | − |
| D-arabinose | + |
| L-arabinose | − |
| D-ribose | + |
| D-xylose | − |
| L-xylose | − |
| D-adonitol | − |
| Methyl-β D-xylopyranoside | − |
| D-galactose | + |
| D-glucose | + |
| D-fructose | + |
| D-mannose | + |
| L-sorbose | − |
| L-rhamnose | − |
| Dulcitol | + |
| Inositol | + |
| D-mannitol | + |
| D-sorbitol | + |
| Methyl-α D-Mannoside | − |
| Methyl-α D-glucoside | − |
| N-acethyl-glucosamine | + |
| Amygdalin | + |
| Arbutin | + |
| Esculin | + |
| Salicin | + |
| D-cellobiose | + |
| D-maltose | + |
| D-lactose | − |
| D-melibiose | − |
| D-sucrose | − |
| D-trehalose | + |
| Inulin | − |
| D-melezitose | + |
| D-raffinose | − |
| Starch | − |
| Glycogen | − |
| Xylitol | − |
| Gentiobiose | + |
| D-turanose | − |
| D-lyxose | − |
| D-tagatose | + |
| D-fucose | − |
| L-fucose | + |
| D-arabitol | − |
| L-arabirol | − |
| Gluconate | + |
| 2-keto-gluconate | − |
| 5-keto-gluconate | − |

As shown in Table 3, the sugar fermentation activity of the MG4272 strain is exhibited for D-ribose, D-galactose, D-glucose, D-fructose, D-mannose, L-sorbose, D-mannitol, D-sorbitol, N-acetyl-glucosamine, amygdalin, arbutin, esculin, salicin, D-cellobiose, D-maltose, D-sucrose, inulin, D-melezitose, gentiobiose, D-turanose, D-tagatose, L-arabirol, and gluconate.

As shown in Table 4, sugar fermentation activity of MG4288 strain is exhibited for D-arabinose, D-ribose, D-galactose, D-glucose, D-fructose D-mannose, dulcitol, inositol, D-mannitol, D-sorbitol, N-acyl-glucosamine, amygdalin, arbutin, esculin, salicin, D-cellobiose, D-trehalose, D-melezitose, gentiobiose, D-tagatose, L-fucose, and gluconate.

Example 9. Measurement of Enzyme Activity of MG4272 and MG4288 Strains

After MG4272 strain or MG4288 strain was streaked on an MRS plate medium and incubated at 37° C. for 24 hours, the resulting colonies were inoculated in MRS liquid medium for stationary culture (37° C., 24 hours). Subsequently, 2% passage in fresh MRS medium was subjected for 24 hours incubation in a stationary manner. After the culture medium was centrifuged (4,000×g, 4° C., 5 minutes), and washed twice with phosphate-buffered saline (phosphate-buffer saline, PBS, pH 7.4). After adjusting the turbidity of the washed cells to 5 to 6 McFarland using 2 mL of Suspension medium (BioMérieux, France), the washed cells were used for the test. The bacterial solution was dispensed into tubes of API ZYM strips, incubated at 37° C. for 4 hours, and then one drop of each of ZYM A and ZYM B reagents (BioMérieux, France) was added thereto. After 5 minutes, enzyme activity was identified through color change. The results of *Lactobacillus paracasei* MG4272 are shown in Table 5, Table 6 shows the results for *Lactobacillus rhamnosus* MG4288.

TABLE 5

| Enzyme assayed for | MG4272 |
|---|---|
| Control (Negative) | − |
| Alkaline phosphatase | − |
| Esterase (C4) | + |

TABLE 5-continued

| Enzyme assayed for | MG4272 |
|---|---|
| Esterase Lipase (C8) | + |
| Lipase (C14) | − |
| Leucine arylamidase | + |
| Valine arylamidase | + |
| Crystinearylamidase | − |
| Trypsin | − |
| α-chymotrypsin | − |
| Acid phosphatase | + |
| Naphtol-AS-BI-phosphohydrolase | + |
| α-galactosidase | − |
| β-glucuronidase | + |
| β-glucosidase | − |
| α-glucosidase | + |
| β-glucosidase | + |
| N-acetyl-β-glucosaminidase | − |
| α-mannosidase | − |
| α-fucosidase | − |

TABLE 6

| Enzyme assayed for | MG4288 |
|---|---|
| Control (Negative) | − |
| Alkaline phosphatase | + |
| Esterase (C4) | + |
| Esterase Lipase (C8) | + |
| Lipase (C14) | − |
| Leucine arylamidase | + |
| Valine arylamidase | + |
| Crystinearylamidase | − |
| Trypsin | − |
| α-chymotrypsin | − |
| Acid phosphatase | + |
| Naphtol-AS-BI-phosphohydrolase | + |
| α-galactosidase | − |
| β-glucuronidase | + |
| β-glucosidase | − |
| α-glucosidase | − |
| β-glucosidase | + |
| N-acetyl-β-glucosaminidase | − |
| α-mannosidase | − |
| α-fucosidase | + |

As shown in Table 5, MG4272 was identified to exhibit enzymatic activity on Esterase (C4), Esterase Lipase (C8), Leucine arylamidase, Valine arylamidase, Acid phosphatase, Naphtol-AS-BI-phosphohydrolase, β-glucuronidase, α-glucosidase, and β-glucosidase.

As shown in Table 6, MG4288 was identified to exhibit enzymatic activity on alkaline phosphatase, Esterase (C4), Esterase Lipase (C8), Leucine arylamidase, Valine arylamidase, Acid phosphatase, Naphtol-AS-BI-phosphohydrolase, β-glucuronidase, β-glucosidase, and α-fucosidase.

Preparation Example of Drug

Compounds according to the present disclosure may be formulated in various forms depending on the purpose. The following are some examples of formulation methods in which a compound according to the present disclosure is included as an active ingredient, but the present disclosure is not limited thereto.

<1-1> Preparation of Powder

MG4272 Strain 2 g of the Present Disclosure

Lactose 1 g

The above ingredients were mixed with each other and the mixture was filled in an airtight cloth to prepare powder.

<1-2> Preparation of Tablets

MG4272 strain 100 mg of the present disclosure

Corn starch 100 mg

Lactose 100 mg

Stearic Acid Magnesium 2 mg

After the above ingredients were mixed with each other, tablets were prepared by tableting the mixture according to a conventional method for preparing tablets.

<1-3> Preparation of Capsule

MG4272 strain 100 mg of the present disclosure

Corn starch 100 mg

Lactose 100 mg

Stearic Acid Magnesium 2 mg

After mixing the above ingredients with each other, the capsules were prepared by filling the mixture in gelatin capsules according to the conventional method for preparing capsules.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

[Accession number]

Depositary: Korea Research Institute of Bioscience and Biotechnology

Accession number: KCTC13822BP

Deposit Date: 20190312

What is claimed is:

1. A composition comprising a cell-free supernatant of *Lactobacillus paracasei* MG4272 strain which was deposited under accession number KCTC13822BP,
   wherein the *Lactobacillus paracasei* MG4272 strain is isolated from the human vagina, and
   wherein the composition has antifungal activity and antimicrobial activity against *Gardnerella vaginalis* and *Candida albicans*.

2. The composition according to claim 1, wherein the *Lactobacillus paracasei* MG4272 strain is stable at pH 3 to pH 4.

3. The composition according to claim 1, wherein the *Lactobacillus paracasei* MG4272 strain is stable at pH 7 to pH 9.

4. The composition according to claim 1, wherein the *Lactobacillus paracasei* MG4272 strain has autoaggregation ability.

5. The composition according to claim 1, wherein the *Lactobacillus paracasei* MG4272 strain has sugar fermentation activity on D-ribose, D-galactose, D-glucose, D-fructose, D-mannose, L-sorbose, D-mannitol, D-sorbitol, N-acetyl-glucosamine, amygdalin, arbutin, esculin, salicin, D-cellobiose, D-maltose, D-sucrose, inulin, D-melezitose, gentiobiose, D-turanose, D-tagatose, L-arabitol, and gluconate.

6. The composition according to claim 1, wherein the *Lactobacillus paracasei* MG4272 strain has enzyme activity of Esterase (C4), Esterase lipase (C8), Leucine arylamidase, Valine arylamidase, Acid phosphatase, Naphtol-AS-BI-phosphohydrolase, β-glucuronidase, α-glucosidase, and β-glucosidase.

7. The composition according to claim 1, wherein the *Lactobacillus paracasei* MG4272 strain is resistant to cefotaxime, cefotetan, kanamycin, streptomycin, nalidixic acid, trimethoprim-sulphamethoxazole, and vancomycin.

8. The composition according to claim 1, wherein the *Lactobacillus paracasei* MG4272 strain has a cell surface exhibiting hydrophobicity.

9. A method of treating an animal having a *Gardnerella vaginalis* infection comprising administering an effective amount of the composition of claim 1.

10. A method of treating an animal having a *Candida albicans* infection comprising administering an effective amount of the composition of claim 1.

11. A method of treating an animal having a vaginitis comprising administering an effective amount of the composition of claim 1.

* * * * *